United States Patent [19]

Nakao

[11] Patent Number: 5,312,908
[45] Date of Patent: May 17, 1994

[54] CHITIN-CHITOSAN OLIGOMER HAVING 2,5-AMHYDROMANNITOL GROUP OR 2,5-ANHYDROMANNOSE GROUP AT TERMINAL END AND METHOD FOR PREPARATION THEREOF

[75] Inventor: Etsuko Nakao, Sapporo, Japan
[73] Assignee: Tamatsukuri Corporation, Hokkaido, Japan
[21] Appl. No.: 912,561
[22] Filed: Jul. 13, 1992

Related U.S. Application Data

[63] Continuation of Ser. No. 572,501, Aug. 23, 1990, abandoned.

[30] Foreign Application Priority Data

Aug. 29, 1989 [JP] Japan ................... 1-222248

[51] Int. Cl.$^5$ .............. C08B 37/08; C08B 37/10; C07H 5/04; C07G 3/00
[52] U.S. Cl. .................... 536/20; 536/55.2; 536/4.1; 536/21
[58] Field of Search ............ 536/20, 55.2, 4.1, 21

[56] References Cited

U.S. PATENT DOCUMENTS

| 3,879,376 | 4/1975 | Vanlerberahe et al. | 536/20 |
| 3,922,260 | 11/1975 | Peniston et al. | 536/20 |
| 4,424,346 | 1/1984 | Hall et al. | 536/20 |
| 4,659,700 | 4/1987 | Jackson | 536/20 |
| 4,788,307 | 11/1988 | Lormeau et al. | 536/21 |
| 4,804,750 | 2/1989 | Nishimura et al. | 536/20 |

FOREIGN PATENT DOCUMENTS 0053612 11/1981 European Pat. Off.
2184002 12/1987 Japan.
220920 7/1968 U.S.S.R.

OTHER PUBLICATIONS

Nippon, S.; Feb. 5, 1989; JA-2292301; Abstract.
F. Yaku et al., Cellulose Chemistry & Technology, II, 421-430 The Preparation of Glucosamine Oligosaccharide and Its Cu(II) Complex (1977).
Hirano et al., Carbohydrate Research, 144 (1985) 338-341, "Preparation of acetylated derivatives of modified chino-oligosaccharides by the depolymerisation of partially N-acetylated chitosan with nitrous acid"(1985).

Primary Examiner—Michael G. Wityshyn
Assistant Examiner—Louise N. Leary
Attorney, Agent, or Firm—Emmanuel J. Lobato; Robert E. Burns

[57] ABSTRACT

A chitin oligosaccharide which is a chitin oligomer having a 2,5-anhydromannose group or a chitosan oligosaccharide which is a chitosan oligomer having a 2,5-anhydromannose group having a structure of the formula shown below at a terminal end:

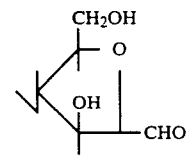

wherein it can be prepared by allowing chitin or chitosan to react with nitrous acid at a temperature of 10° C. or lower in an aqueous solution with a hydrogen ion concentration of 1 to 6 to effect deamination reaction and pinacol rearrangement reaction, and further reducing this with a reducing agent, a chitin oligosaccharide which is a chitin oligomer having a 2,5-anhydromannitol group or a chitosan oligosaccharide which is a chitosan oligomer having a 2,5-anhydromannitol group having a structure of the formula shown below at an end:

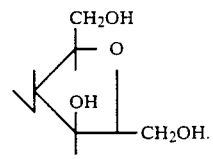

7 Claims, 11 Drawing Sheets

CHITIN-CHITOSAN OLIGOMER HAVING 2,5-AMHYDROMANNITOL GROUP OR 2,5-ANHYDROMANNOSE GROUP AT TERMINAL END AND METHOD FOR PREPARATION THEREOF

This is a continuation of application Ser. No. 07/572,501, filed Aug. 23, 1990, now abandoned.

BACKGROUND OF THE INVENTION

1. Field of the Art

This invention relates to a method for preparing a chitin oligomer or a chitosan oligomer and for preparing a chitosan oligosaccharide which is a mixture of chitin oligomers or a chitosan oligosaccharide which is a mixture of chitosan oligomers at high yield from chitin or chitosan.

2. Related Art

In recent years, food life has become rich, and crabs, prawns are imported from abroad, and from the chitin material of their shells, chitin and chitosan have been produced in large amounts. Chitin and chitosan are themselves now under development as agricultural chemicals, artificial skin, life-related substances, etc., and chitin oligosaccharide or chitosan oligosaccharide which is of further added value is now attracting attention.

It has been known in the art that such chitin oligosaccharide or chitosan oligosaccharide can be generally prepared by degradation with chitin with chitinase or chitosan with chitosanase.

It has been also known that chitin and chitosan can be partially hydrolyzed with hydrochloric acid to prepare from N-acetylglucosamine or glucosamine, N-acetylchitopentaose or chitopentaose.

On the other hand, a method is also known of utilizing the Van Slyke Method quantitating amino-form nitrogen, in which chitosan is depolymerized by addition of nitrous acid to chitosan at a temperature of 20° to 25° C. (U.S. Pat. No. 3,922,260).

However, the above degradation method with an enzyme can control the molecular weight with difficulty, whereby an oligosaccharide mixture having various molecular weights is obtained, and yet the concentration is as dilute as 0.001% and therefore must be concentrated. Accordingly, for obtaining an oligosaccharide with an adequate molecular weight, fractionation must be carried out which is extremely cumbersome laborious, and also since oligosaccharide with a terminal end of the structure as follows:

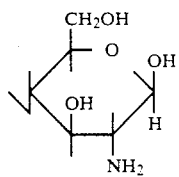

is formed, when heated in the concentration operation or sterilization operation, a Maillard reaction may occur which causes coloration. Also, even if this may be further reduced with a reducing agent, there is the problem that it may be subjected to ring opening to be converted to a sugar alcohol. Besides, this method employs a dilute reaction concentration, and large scale equipment is required for bulk production.

Also, since the above-mentioned method of partially hydrolyzing with hydrochloric acid gives the same product as the above enzyme, the problems of coloration, ring opening as mentioned above cannot be solved.

On the other hand, the latter method of depolymerizing chitosan with nitrous acid, partly because chitosan with an extremely high molecular weight is used, requiring nitrous acid employed to be added in of as much as 3 to 5 moles per 1 mole of the amino groups of the chitosan, whereby it may be degraded to glucosamine which is a monosaccharide. Alternatively, since the decomposition reaction is carried out at a relatively high temperature of 20° to 25° C., side reactions such as transfer reaction may occur before degradation to monosaccharides, and these reaction products may be recombined to form products other than chitosan oligosaccharides.

Accordingly, in the product obtained by such a method, recombined glucoside compounds may be present, other than the above-mentioned glucosamine, which may exhibit toxicity; also unreacted nitrous acid is mixed in the product, whereby there are problems for use as food additives or pharmaceuticals.

SUMMARY OF THE INVENTION

The present inventor has intensively studied to the problems described above, and consequently found that a chitin oligosaccharide which is a chitin oligomer having 2,5-anhydromannose group or a chitosan oligosaccharide which is a chitosan oligomer having a 2,5-anhydromannose group with a structure of the formula shown below at a terminal end:

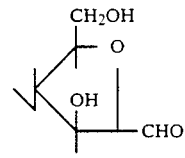

can be prepared by allowing chitin or chitosan to react with nitrous acid at a temperature of 10° C. or lower in an aqueous solution with a hydrogen ion concentration (pH) of 1 to 6 to effect a deamination reaction and pinacol rearrangement reaction, and further reducing this with a reducing agent, whereby a chitin oligosaccharide is formed which is a chitin oligomer having 2,5-anhydromannitol group or a chitosan oligosaccharide is formed which is a chitosan oligomer having a 2,5-anhydromannitol group having a structure of the formula shown below at an end:

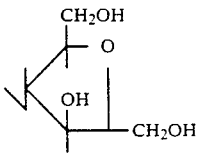

to accomplish the present invention.

That is, the chitin oligomers of the present invention are chitin oligomers having a 2,5-anhydromannitol group at a terminal end, comprising a 2,5-anhydromannitol group of the structural formula:

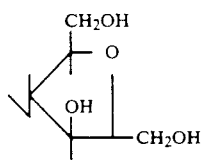

at one end and a group of the structural formula:

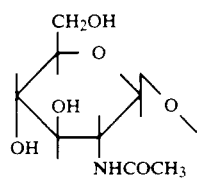

at the other end, both of these ends being bonded directly or through a chain of 0 to 1,000 units of the structural formula:

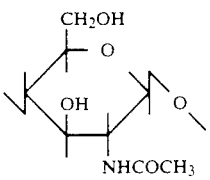

said chain optionally containing as a part thereof a unit of the structural formula:

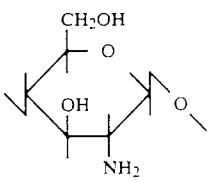

and a chitin oligomer having a 2,5-anhydromannose group at a terminal end, comprising a 2,5-anhydromannose group of the structural formula;

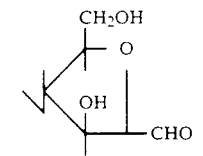

at one end and a group of the structural formula:

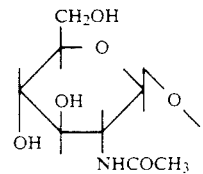

at the other end, both of these ends being bonded directly or through a chain of 0 to 1,000 units of the structural formula:

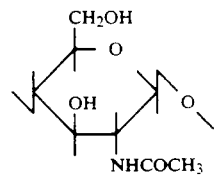

said chain optionally containing as a part thereof the unit of the formula:

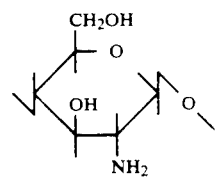

On the other hand, the chitosan oligomers which constitute another embodiment of invention are chitosan oligomers having 2,5-anhydromannitol group at a terminal end, comprising 2,5-anhydromannitol group of the structural formula:

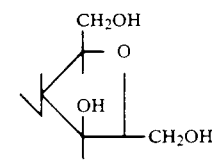

at one end and a group of the structural formula:

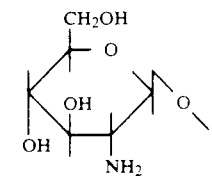

at the other end, both of these ends being bonded directly or through a chain of 0 to 500 units of the structural formula;

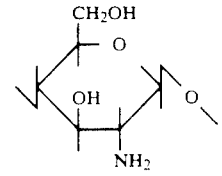

said chain optionally containing as a part thereof a unit of the structural formula:

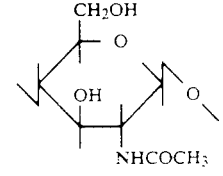

and a chitosan oligomer having a 2,5-anhydromannose group at a terminal end, comprising a 2,5-anhydromannose group of the structural formula:

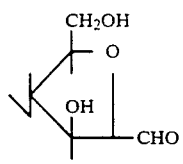

at one end and a group of the structural formula:

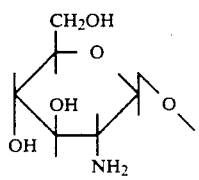

at the other end, both of these ends being bonded directly or through a chain of 0 to 500 units of the structural formula:

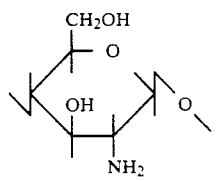

said chain optionally containing as a part thereof a unit of the structural formula:

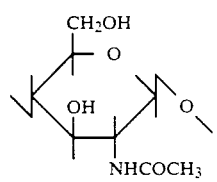

Further, the method for preparing a chitin or chitosan oligomer which is still another embodiment of the present invention comprises allowing chitin or chitosan to react with nitrous acid at a temperature of 10° C. or lower in an aqueous solution with a hydrogen ion concentration of 1 to 6.

Also, the method for preparing a chitin oligomer or a chitosan oligomer having 2,5-anhydromannitol which is another embodiment of the present invention comprises reducing a chitin oligomer or a chitosan oligomer having a 2,5-anhydromannose group at a terminal end with a reducing agent.

The chitin oligomer or chitosan oligomer of the present invention, which has a 2,5-anhydromannose group of the structure:

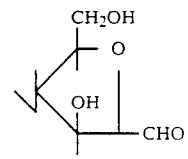

can be bound to another compound, and therefore can be utilized as the starting material or the intermediate for food additives or pharmaceuticals.

On the other hand, chitin oligomer or chitosan oligomer having 2,5-anhydromannitol of the structure:

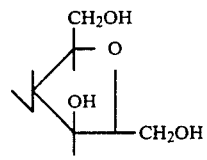

which is low in reactivity, high in stability and therefore colored with difficulty, can be utilized as such as the starting material or the intermediate for food additives or pharmaceuticals, etc.

DETAILED DESCRIPTION OF THE INVENTION

[I] Chitin.chitosan oligomer (1) Chitin oligomer

Figure 1:
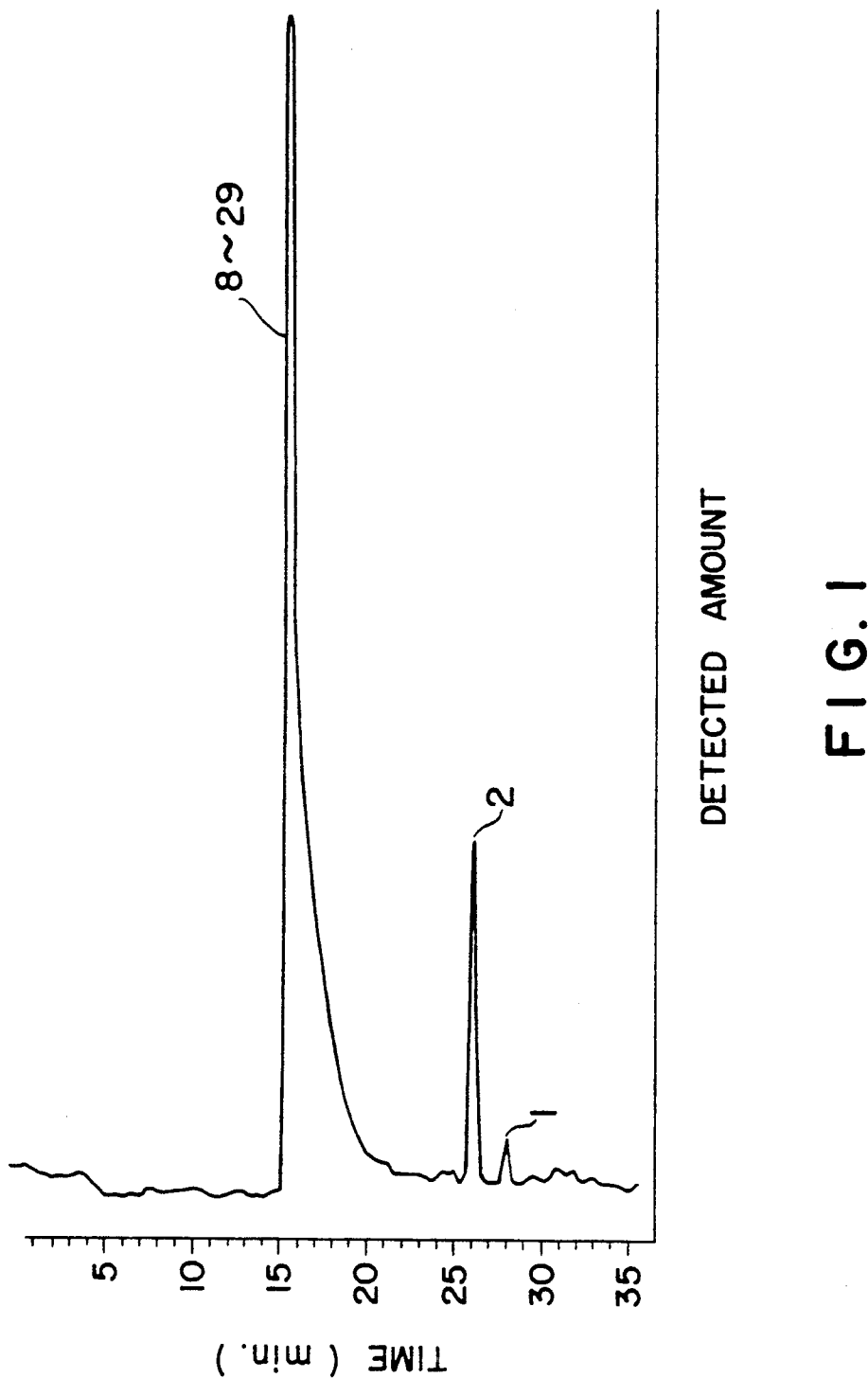

As the chitin oligomer in the present invention, there may be included one having a 2,5-anhydromannitol group at a terminal end, comprising a 2,5-anhydromannitol group of the structural formula:

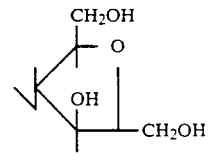

at one end and a group of the structural formula:

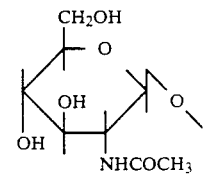

at the other end, both of these ends being bonded directly or through a chain of 0 to 1,000, preferably 0 to 500, particularly 40 to 250 units of the structural formula:

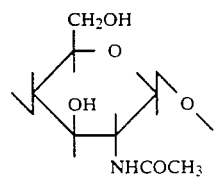

said chain optionally containing the unit of the structural formula at a ratio in the range of 50% or less, preferably 45% or less:

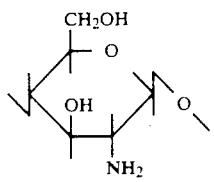

and one having 2,5-anhydromannose group at a terminal end, comprising 2,5-anhydromannose group of the structural formula:

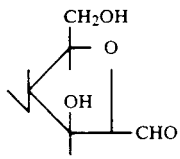

at one end and a group of the structural formula:

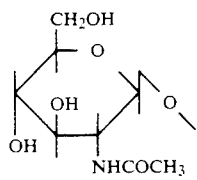

at the other end, both of these ends being bonded directly or through a chain of 0 to 1,000, preferably 0 to 500, particularly 40 to 250 units of the structural formula:

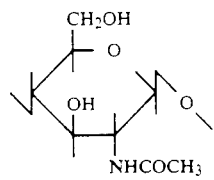

said chain optionally containing a unit of the structural formula at a ratio in the range of 50% or less, preferably 45% or less:

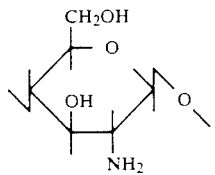

The above-mentioned chitin oligomer has a 2,5-anhydromannitol group at a terminal end, comprising a 2,5-anhydromannitol group of the structural formula:

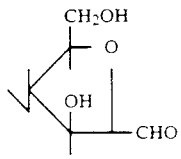

at one end and a group of the structural formula:

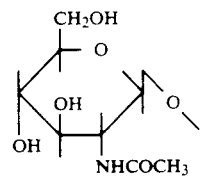

at the other end, both of these ends being bonded directly or through a chain of 0 to 1,000 units of the structural formula:

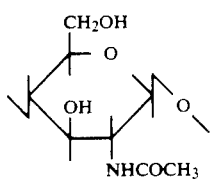

but, since those containing amino groups partially acetylated are generally contained in the naturally occurring chitin, alternatively by use of artificially deacetylated chitin, a chitin oligomer of chitosan oligomer can be also made with a part of the chain in the above structural formula being converted to a chain of the formula:

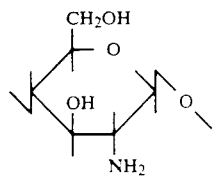

Therefore, it is difficult to discriminate between the deacetylated chitin oligomer and chitosan oligomer.

However, generally speaking, a chitin oligomer has a molecular weight ranging from about 570 to 200,000 and a deacetylation degree ranging from 0 to 50%, while a chitosan oligomer has a molecular weight ranging from about 480 to 100,000 and a deacetylation degree ranging from 50 to 100%.

The above chitin oligomer having a 2,5-anhydromannose group has the structural formula shown below at a terminal end:

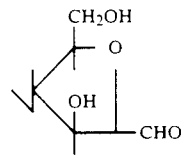

and therefore is rich in reactivity, having the advantage that it can be reacted with various compounds.

Thus, it can be used as the starting material or the intermediate for various pharmaceuticals.

However, while it is rich in reactivity, it is on the other hand unstable to heat and hence has the drawback of being readily colored, and therefore it can be reduced with a reducing agent to convert the structural formula:

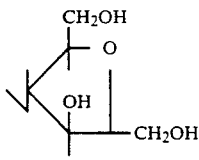

at the terminal end to 2,5-anhydromannitol, thereby forming a thermally stable chitin oligomer with reduced reactivity.

Even if the above 2,5-anhydromannose group may be reduced to 2,5-anhydromannitol group, since the structural formula at the other end and the structural formula of the intermediate chain remain unchanged, the primary properties useful for pharmaceuticals, food additives will not change, whereby there is substantially no change in usefulness.

(2) Chitosan oligomer

As the chitosan oligomer in the present invention, there is one having a 2,5-anhydromannitol group at a terminal end, comprising a 2,5-anhydromannitol group of the structural formula:

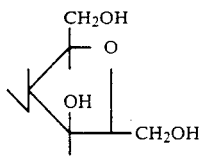

at one end and a group of the structural formula:

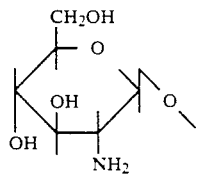

at the other end, both ends being bonded directly or through a chain of 0 to 500, preferably 0 to 300, particularly 0 to 30 units in the case of one with low molecular weight or 40 to 280 units in the case of one with high molecular weight, of the structural formula:

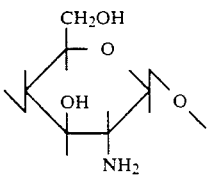

containing optionally as a part of the chain generally 50% or less, preferably 45% or less of the structural units represented by the formula:

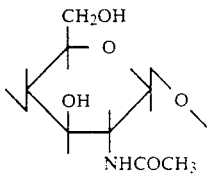

and one having 2,5-anhydromannose group at a terminal end, comprising a 2,5-anhydromannose group of the structural formula:

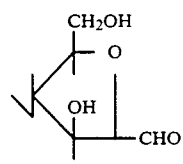

at one end and a group of the structural formula:

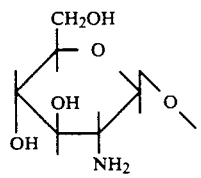

at the other end, both ends being bonded directly or through a chain of 0 to 500, preferably 0 to 300, particularly 0 to 30 units in the case of one with low molecular weight or 40 to 280 units in the case of one with high molecular weight, of the structural formula:

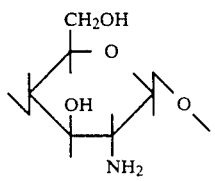

containing optionally as a part of the chain generally 50% or less, preferably 45% or less of the structural units represented by the formula:

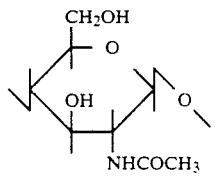

The above-mentioned chitosan oligomer has a 2,5-anhydromannitol group of the structural formula:

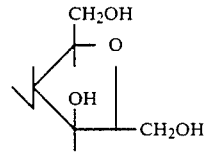

or a 2,5-anhydromannose group of the formula:

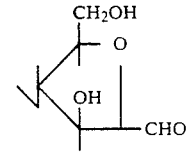

at one end and a group of the structural formula:

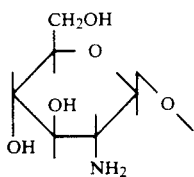

at the other end, both ends being bonded directly or through a chain of 0 to 500 units of the structural formula;

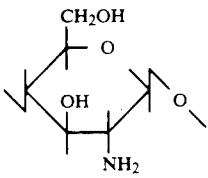

but, since those containing amino group partially acetylated are generally contained in the naturally occurring chitosan, alternatively by use of artificially deacetylated chitosan, a chitosan oligomer containing the structural formula shown below may be also formed:

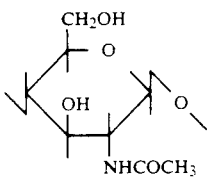

The above chitosan oligomer having a 2,5-anhydromannose group has the structural formula shown below at a terminal end:

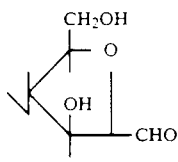

and therefore is rich in reactivity, having the advantage that it can be reacted with various compounds.

Thus, it can be used as the starting material or the intermediate for various pharmaceuticals.

However, while it is rich in reactivity, it is on the other hand unstable to heat and hence has the drawback of being readily colored, and therefore it can be reduced with a reducing agent to convert the structural formula:

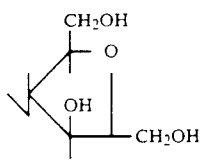

at the terminal end to 2,5-anhydromannitol, thereby forming a thermally stable chitosan oligomer with reduced reactivity.

Even if the above 2,5-anhydromannose group may be reduced to 2,5-anhydromannitol group, since the structural formula at the other end and the structural formula of the intermediate chain remain unchanged, the primary properties useful for pharmaceuticals, food additives will not change, whereby there is substantially no change in usefulness.

[II] Method for preparing chitin.chitosan oligomer (1)

Starting materials (a) Chitin.chitosan

Chitin and chitosan to be used for preparation of chitin.chitosan oligomer of the present invention is the chitin obtained by treating the chitin material contained as the constituent of crustaceans such as prawns, crabs, etc., insects such as beetles, crickets, etc., shiitake (mushroom), the cell walls of molds, hydrochloric acid to remove calcium carbonate and then treating it with an alkali solution for a short time to remove proteins, etc., or the chitosan obtained by heating this with a conc. alkali to effect deacetylation.

Generally, these naturally occurring chitins have an average molecular weight of 100,000 to some 1,000,000, with the average molecular weight of chitosan being as high as about 20,000 to about 200,000, and therefore if these naturally occurring chitin.chitosan are used as such as the starting material, they are so viscous that no sufficient reaction with nitrous acid can be effected unless it is carried out under severe conditions.

Hence, the chitin.chitosan oligomer obtained by the reaction under such severe conditions is only a mixture containing various molecular weights in which high molecular weights and low molecular weights exist mixed therein, because said reaction is susceptible to occur from the surface of the starting material molecules. Therefore, for obtaining a chitin.chitosan oligomer with a uniform molecular weight, it is preferable to use one with low viscosity having an average molecular weight of 50,000 or lower, preferably 20,000 to 50,000, particularly 30,000 to 40,000 for the chitin or chitosan to be used as the starting material.

In the method for preparing the chitin or chitosan of the present invention, since the reaction is caused to occur by alcoholization of the amino groups in the chitin with nitrous acid, it is common to use chitin containing amino groups.

However, since 3 to 10% of units having amino groups are generally contained in the naturally occurring chitins, the reaction is carried out in the present invention by use of them, but alternatively, the chitins or chitosans obtained by partial or total deacetylation may be employed.

These chitins or chitosans should be preferably solubilized in order to carry out the reaction of the present invention smoothly. Therefore, it is preferable to use those in fine powdery form, particularly in flakes of 15 to 30 mesh pass, preferably 30 mesh pass.

(b) Nitrous acid

As the nitrous acid to be used in the present invention, nitrous acid may be also used as such, but for the purpose of permitting the reaction to proceed slowly, it is preferable to use a nitrite which can give nitrous acid in situ.

Examples of such nitrite may include sodium nitrite, potassium nitrite, zinc nitrite, ammonium nitrite, calcium nitrite, barium nitrite, magnesium nitrite, etc., and among them it is preferable to use an alkali metal nitrite, particularly sodium nitrite, potassium nitrite.

These nitrites are used to alcoholize the amino groups in the chitin or chitosan by deamination, and therefore generally are used in amounts within the range from 0.01 to 1 mole equivalent, preferably 0.1 to 0.6 mole equivalent relative to amino groups, and the molecular weight of the chitin oligomer or the chitosan oligomer formed can be controlled depending on the amount. If the amount used is less than 0.01 mole equivalent, the reaction will occur with difficulty, while if it is above 1 mole equivalent, monosaccharides such as N-acetylglucosamine or glucosamine are liable to be formed in large amounts, whereby the yield of the chitin oligomer or the chitosan oligomer will be lowered.

(2) Reaction (a) Solubilization

In preparing the chitin oligomer or the chitosan oligomer of the present invention, to make it easier to carry out the reaction of the chitin and the chitosan which are the starting materials, it is preferable to solubilize the chitin or the chitosan in an aqueous solution by mixing with a solubilizing agent in the reaction aqueous medium for these chitin and chitosan.

reaction as described below is controlled within a specific range.

(b) Reaction

In preparing the chitin oligomer or the chitosan oligomer of the present invention, an important point is that the chitin or the chitosan should be allowed to react in a mixture with nitrous acid at a temperature of 10° C. or lower, preferably −5 to 10° C., more preferably 0 to 8° C., particularly 2° to 6° C., in an aqueous solution with a hydrogen ion concentration (pH) of 1 to 6, preferably 2 to 4.

By mixing under such conditions, the reaction proceeds slowly, and therefore the chitin or the chitosan is not hydrolyzed at the glycoside bound portion where glucosaminoglucan unit is bonded, but the amino group in the chitin or the chitosan is alcoholized by deamination with nitrous acid, and the alcohol group constitutes a pseudo glycol more adjacent to the oxygen at the glycoside bound portion of the glucosaminoglucan unit, whereby it is estimated that the pinacol rearrangement reaction as shown below may have probably occurred.

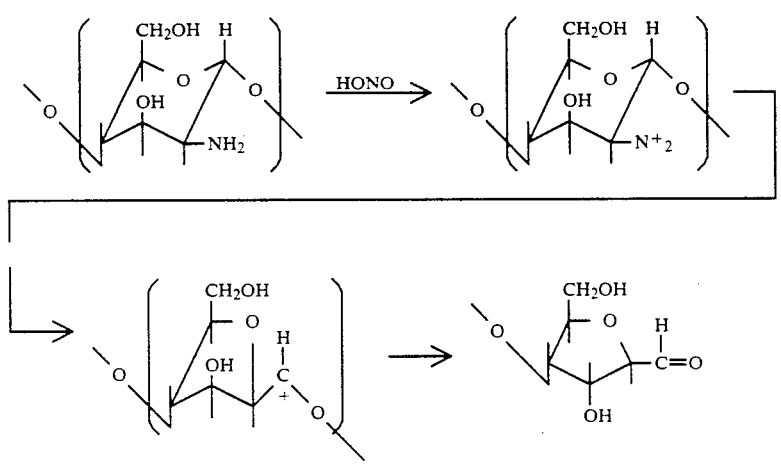

Solubilizing Agent

As the solubilizing agent to be used for solubilizing the above chitin and chitosan, there can be included organic acids having 1 to 10 carbon atoms, preferably 2 to 7 carbon atoms, such as formic acid, acetic acid, butyric acid, oxalic acid, tartaric acid, succinic acid, lactic acid, ascorbic acid, propionic acid, adipic acid, benzoic acid, etc., mineral acids such as hydrochloric acid, hydrobromic acid, nitric acid, etc. Among them, acetic acid, oxalic acid, tartaric acid, lactic acid are preferred, and it is particularly suitable to use acetic acid.

These solubilizing agents can be used either individually or as a mixture, but generally are used as a mixture with water which is the reaction solvent.

These solubilizing agents may be employed in amounts of 0.5 mole % or more, preferably equimolar % or more relative to the chitin or the chitosan, but since a greater amount is permissible, they are generally employed in amounts not more than 20 vol.% of water, preferably 0.1 to 20 vol. %, particularly 5 to 10 vol. % of water which is the reaction solvent.

By controlling the kind and the amount of the solubilizing agent, the hydrogen ion concentration in the If the reaction temperature in the above reaction conditions exceeds 10° C., a hydrolysis reaction will occur, and further a transfer reaction and recombination occur, whereby there is a fear that toxic glycoside units may be formed. On the other hand, when the hydrogen ion concentration is less than 1, the hydrolysis reaction which effects cleavage of the glycoside bond is liable to occur, whereby a transfer reaction and recombination may be caused to occur. If the hydrogen ion concentration exceeds 6, nitrous acid will be decomposed to lose the effect, or the molecular weight cannot be controlled.

The above-mentioned reaction is carried out in an aqueous solution under the conditions of the above-mentioned temperature and hydrogen ion concentration, but other organic solvents and buffers can be also mixed into said aqueous solution.

The reaction is commonly carried out generally for several minutes to 10 hours, preferably for about 0.5 to 3 hours. (c) Neutralization The mixture of the chitin oligomer or the chitosan oligomer having a 2,5-anhydromannose group at a terminal end containing nitrous acid or a nitrite obtained by the above reaction contains a large amount of unreacted nitrous acid or a nitrite, and therefore exhibits strong acidity, and because various problems will occur if the reaction in the subsequent step is attempted while containing nitrous acid or nitrite under such state, it is important to neutralize the mixture.

Such neutralization may be effected to a hydrogen ion concentration (pH) of 7 or higher, preferably about 7 to 8 by addition of a neutralization agent.

Said neutralization can make it easier to carry out the subsequent reaction and also to precipitate the chitin oligomer or the chitosan oligomer formed.

As the neutralization agent to be added, various agents including alkalis such as caustic soda can be included, but it is desirable to use ammonia, an alkylamine or an anion exchange resin, and specific examples thereof can be set forth below.

Ammonia

As the above-mentioned ammonia, conc. ammonia water which is an ammonia water having ammonia gas dissolved in water, generally with a concentration of 20 to 30% by weight, preferably 26 to 30% by weight, can be employed.

The amount of said ammonia added may be up to the level where the hydrogen ion concentration in the above-mentioned aqueous medium is within the range as specified above, specifically an amount generally of 40 to 70 milliliters ammonia water/liter-reaction mixture.

Alkylamines

As the alkylamines as mentioned above, there can be included amines of alkyl groups having 1 to 20 carbon atoms such as methylamine, ethylamine, diethylamine, triethylamine, n-propylamine, isopropylamine, n-butylamine and the like.

The amount of said alkylamines may be up to the level where the hydrogen ion concentration in the above-mentioned aqueous medium is within the range as specified above, but specifically an amount generally of 50 to 200 g/liter-reaction mixture.

Anion Exchange Resin

As the above-mentioned anion exchange resin, resins having basicity such as amino group ($-NH_2$, $-NHR$, $-NR_2$), quaternary ammonium group ($-^+NR_3$), etc. introduced into the matrix of synthetic resins can be included.

As the amount of said anion exchange resin added, it is added until acids such as nitrous acid as mentioned above is neutralized, specifically in an amount generally of 200 g/liter or more, preferably 300 g to 1 kg/liter or more based on the reaction mixture.

(3) Reduction reaction

In the neutralized mixture as described above, chitin or chitosal oligomer having 2,5-anhydromannose groups is present, and said oligomer has an aldehyde group with high reactivity of the structural formula at a terminal end of:

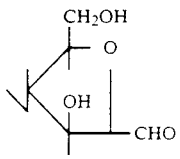

and therefore is rich in reactivity, thus having the drawback of being readily colored or combined, and can be reduced to an alcohol to make the structural formula at the terminal end 2,5-anhydromannitol of the formula:

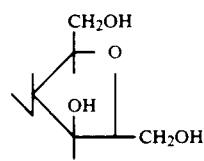

thereby making a stable chitin or chitosan oligomer with reduced reactivity.

For such reduction reaction, any of the reducing agents known in the art which can gently reduce aldehyde groups can be chosen. Specifically, there can be included nickel type catalysts for hydrogenation reduction such as Raney nickel, Ni-carbon, etc., palladium type catalysts for hydrogenation reduction such as Pd-carbon, metal hydrides such as aluminum diisobutyl hydride, organic tin hydrides, hydrosilane and the like; metal hydrogen complex compounds such as lithium aluminum hydride, sodium boron hydride, potassium boron hydride, lithium boron hydride, calcium boron hydride, zinc boron hydride and the like; diborane, alkylborane and the like.

Among these reducing agents, particularly preferable reducing agents can include metal hydrides such as aluminum diisobutyl hydride, organic tin hydrides, hydrosilane, etc., metal hydrogen complex compounds such as lithium aluminum hydride, sodium boron hydride, potassium boron hydride, lithium boron hydride, calcium boron hydride, zinc boron hydride and the like, diborane, alkylboranes, etc. Among them, it is most suitable to use metal hydrogen complex compounds, particularly boron hydride compounds such as sodium boron hydride, potassium boron hydride and the like.

Such reduction reaction is carried out by adding the above reducing agent into said neutralized mixture as such or after removal of the impurities in said neutralized mixture simply by filtration, etc.

The reducing agent may be added at a ratio generally of 1 mole or more, preferably 1.5 to 3 moles, per one mole of 2,5-anhydromannose group in the chitin oligomer or the chitosan oligomer to reduce the 2,5-anhydromannose group in the chitin oligomer or the chitosan oligomer to a 2,5-anhydromannitol group.

Said reduction reaction may be carried out at a temperature generally of 100° C. or lower, preferably room temperature or lower, generally under normal pressure for several hours.

Said reduction reaction is carried out until there exists substantially no 2,5-anhydromannose group.

(4) Fractionation

Into an aqueous medium in which chitin oligomers or chitosan oligomers with different molecular weights having 2,5-anhydromannitol group at an end as described above, a solvent for precipitation which is compatible with said aqueous medium and can dissolve the above-mentioned chitin oligomers or chitosan oligomers with difficulty is added gradually or stepwise, thereby precipitating the chitin chitosan oligomers by fractionation from the above-mentioned aqueous medium successively in the order from one having larger molecular weight. By this fractionation operation, fractions with a narrow molecular weight distribution can be obtained.

(a) Addition of precipitation medium

When neutralization is effected with the use of ammonia water, an alkylamine or an anion exchange resin as the neutralizing agent as described above, the chitin oligomer or the chitosan oligomer having 2,5-anhydromannose formed from the aqueous medium is susceptible to precipitation, and therefore by adding further a medium for precipitation which is compatible with said aqueous medium and can dissolve said chitin oligomer or chitosan oligomer with difficulty gradually or stepwise, the chitin oligomers of chitosan oligomers are precipitated from the above-mentioned aqueous medium successively in the order from one having larger molecular weight.

(b) Medium for precipitation

As the medium which is compatible with said aqueous medium and can dissolve the above-mentioned chitin oligomers or chitosan oligomers with difficulty, for example, alcohols, ketones, ethers, esters, hydrocarbons and others can be included.

Specifically, there are alcohols having 1 to 5, preferably 1 to 4 carbon atoms such as methanol, ethanol, propanol, butanol, ethylene glycol and the like; ketones having 1 to 5, preferably 1 to 4 carbon atoms such as acetone, methyl ethyl ketone and the like; ethers having 2 to 6, preferably 2 to 4 carbon atoms such as ethyl ether and the like; esters having 2 to 10, preferably 2 to 5 carbon atoms such as ethyl acetate and the like; hydrocarbons having 1 to 10, preferably 1 to 6 carbon atoms such as n-hexane, petroleum ether, etc.

(c) Amount added

The amount of these precipitating media added may be that which can precipitate chitin oligomers or chitosan oligomers with larger molecular weights from the above-mentioned aqueous medium, and more specifically may be generally 0.4 to 1.5 liter, preferably 0.5 to 1 liter per 1 liter of the above-mentioned aqueous medium.

By fractionating the chitin oligomers or chitosan oligomers thus precipitated successively, the chitin oligosaccharides or the chitosan oligosaccharides can be fractionated for respective various polysaccharides with various larger molecular weights.

(5) Product

By isolating the chitin oligosaccharide or the chitosan oligosaccharide with a constant molecular weight obtained by fractionation for respective various polysaccharides, each fraction contains a chitin oligosaccharide or a chitosan oligosaccharide with a molecular weight of high efficacy, whereby still higher effect can be exhibited.

On the other hand, the chitin oligomers or the chitosan oligomers having a 2,5-anhydromannitol group at the reduced terminal end side is lower in reactivity, high in thermal stability, and therefore will be colored with difficulty and useful as such as the food additive or pharmaceutical, or as the intermediate therefore.

Further, with the chitin oligomer or the chitosan oligomer of the present invention thus obtained under the state with a 2,5-anhydromannose group being reduced to 2,5-anhydromannitol group which is also thermally stable, nitrous acid is neutralized sufficiently in a mixture, and a precipitation medium which is a poor solvent for the chitin oligomer or the chitosan oligomer under the state in which said nitrous acid is dissolved in water is gradually added to precipitate and recover only the chitin oligomer or the chitosan oligomer dissolved in said mixture. Accordingly, in the chitin oligomer or the chitosan oligomer, nitrous acid or a nitrite is contained only in an amount generally of about 20 ppm or less, preferably 2 ppm or less, particularly 0 to 0.7 ppm, which is lower than the level of 25 ppm as defined by Food Law, and therefore it will not be restricted also in development of uses for preparation of food additives and pharmaceuticals.

EXAMPLES

Example 1

Into a glass flask of 5-liter inner volume equipped with a stirrer was charged 100 g of a chitosan in flakes of 30 mesh pass, and 2 liters of 10% aqueous acetic acid were added little by little to dissolve the chitosan, followed by sufficient cooling of the solution in an ice-bath to 4° C.

Subsequently, 300 milliliters of 1% aqueous sodium nitrite (nitrous acid/glucosamine residue=molar ratio 0.1) was added to adjust the hydrogen ion concentration (pH) to 3, and the reaction was carried out under stirring at 4° C. for 1.5 hours to prepare a chitosan oligomer having 2,5-anhydromannose group.

After completion of the reaction, the mixture was neutralized with 393 milliliters of conc. ammonia water, and further with addition of 3.2 g of sodium boron hydride (2-fold moles relative to sodium nitrite), the reduction reaction was carried out with stirring in an ice-water bath for 5 hours to prepare a chitosan oligomer having 2,5-anhydromannitol.

After completion of the reduction reaction, for making the product readily precipitatable, conc. ammonia water was added to control mixture to pH 8, followed by addition of 2.5 liters of acetone to precipitate the product.

The precipitates were filtered, thoroughly washed with acetone, dried in a vacuum oven and then analyzed by high performance liquid chromatography and elemental analysis.

The analytical conditions in high performance liquid chromatography are as follows:
Column: Asahipack GS-220
Flow rate: 0.5 milliliters/min.
Temperature: 50° C.
Mobile phase: 0.5M acetate buffer
pH: 4.0.

The results are shown in FIG. 1. The product contained 1.0% of monosaccharides, 6.9% of disaccharides and 80.6% of 8-29 saccharides, and the yield of the product was 59.7 g, which was found to be 60% of the theoretical yield 99.4 g.

Example 2

By use of the same glass flask equipped with a stirrer, 100 g of a chitosan was added and dissolved by adding one liter of 10% aqueous acetic acid little by little and then cooled sufficiently with ice-water.

Subsequently, to the solution was added 88 milliliters of 10% aqueous sodium nitrite (nitrous acid/glucosamine residue=molar ratio 0.3) to adjust the hydrogen ion concentration (pH) to 3, and the reaction was carried out in an ice-water bath for 4 hours.

After completion of the reaction, the mixture was neutralized with 210 milliliters of conc. ammonia water, and further 9.6 g of sodium boronhydride (2-fold moles relative to sodium nitrite) was added to carry out the reduction reaction with stirring in an ice-water bath for 4 hours.

After completion of the reduction reaction, in order to make the product readily precipitatable, conc. ammonia water was added to control the mixture to pH 8 to 9, followed by concentration to ½ volume (about 500 milliliters).

Figure 2:
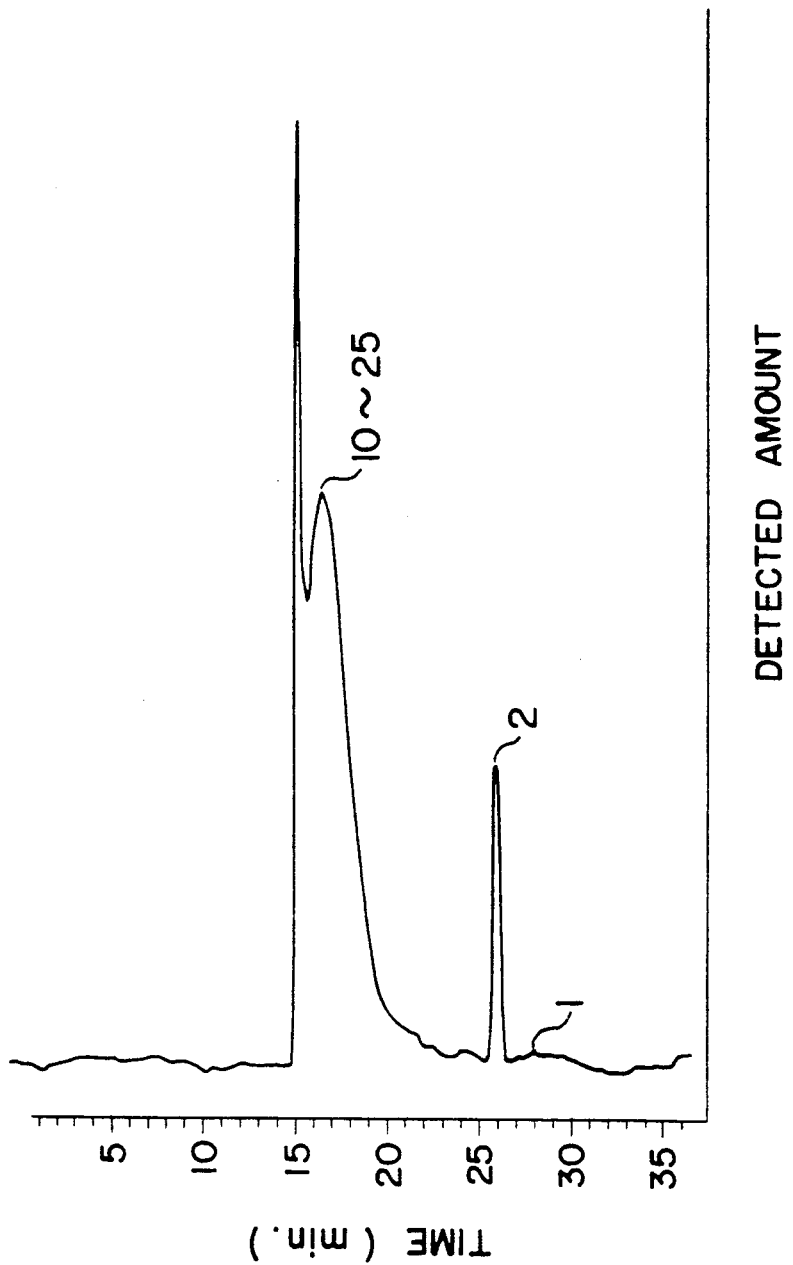

Subsequently, to the concentrate was added 3.5 liters of methanol, and the precipitates formed were filtered and analyzed by high performance liquid chromatography to obtain the results shown in FIG. 2. The precipitates were found to contain 0.2% of 5 monosaccharides, 5.3% of disaccharides and 69.3% of 10-25 saccharides.

Figure 3:
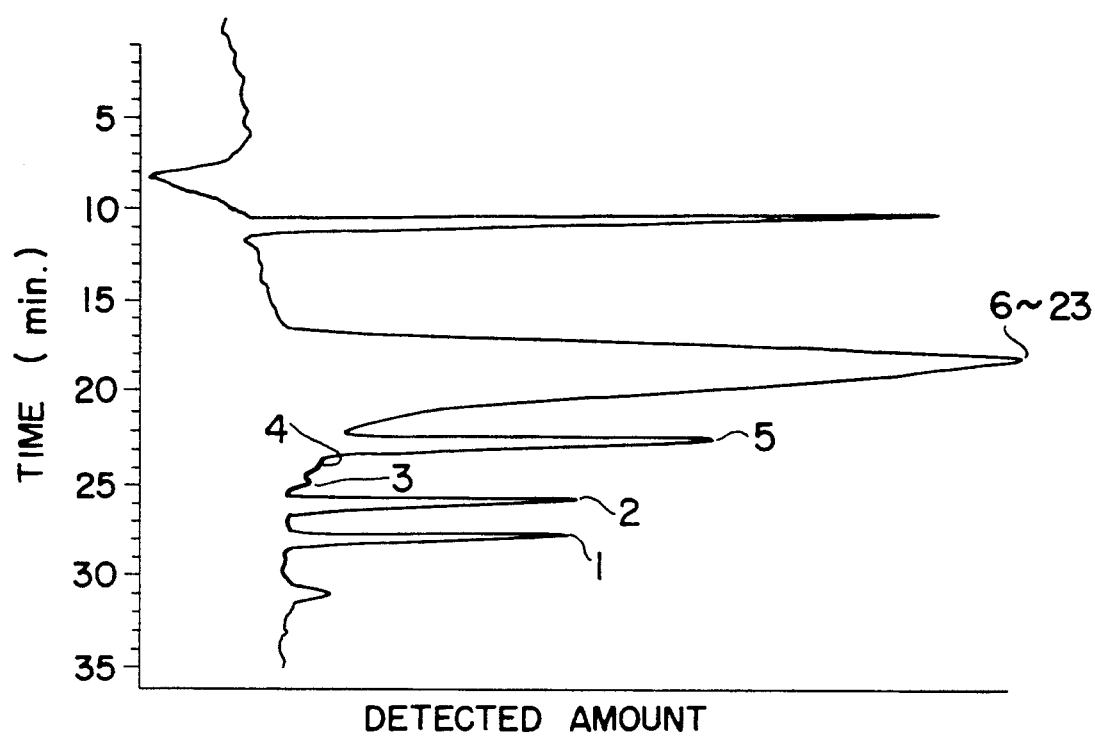

Said filtrate was further concentrated, a mixture of methanol-acetone (1:1) added to the concentrate to effect precipitation again, and the precipitates were analyzed again by high performance liquid chromatography to obtain the results shown in FIG. 3. The precipitates were found to contain 3.7% of monosaccharides, 4.1% of disaccharides, 0.2% of trisaccharides, 0.1% of tetrasaccharides, 10.4% of pentasaccharides and 67.5% of 6-23 saccharides.

As the result, the yield of the product was 74.3 g, which corresponded to 76% of the theoretical yield 98.2 g.

Example 3

By use of the same glass flask equipped with a stirrer, 100 g of a chitosan was added and further dissolved by adding one liter of 10% aqueous acetic acid little by little and then cooled sufficiently with ice-water.

Subsequently, to the solution was added 146 milliliters of 10% aqueous sodium nitrite (nitrous acid/glucosamine residue = molar ratio 0.5) to adjust the hydrogen ion concentration (pH) to 3, and the reaction was carried out in an ice-water bath for 4 hours.

After completion of the reaction, the mixture was neutralized with 220 milliliters of conc. ammonia water, and further 16.0 g of sodium boronhydride (2-fold moles relative to sodium nitrite) was added to carry out the reduction reaction with stirring in an ice-water bath for 4 hours.

After completion of the reduction reaction, in order to make the product readily precipitatable, conc. ammonia water was added to control the mixture to pH 8 to 9, followed by concentration to ½ volume (about 500 milliliters).

Subsequently, to the concentrate was added 1.5 liters of methanol, and the precipitates formed were filtered and washed with acetone.

Figure 4:
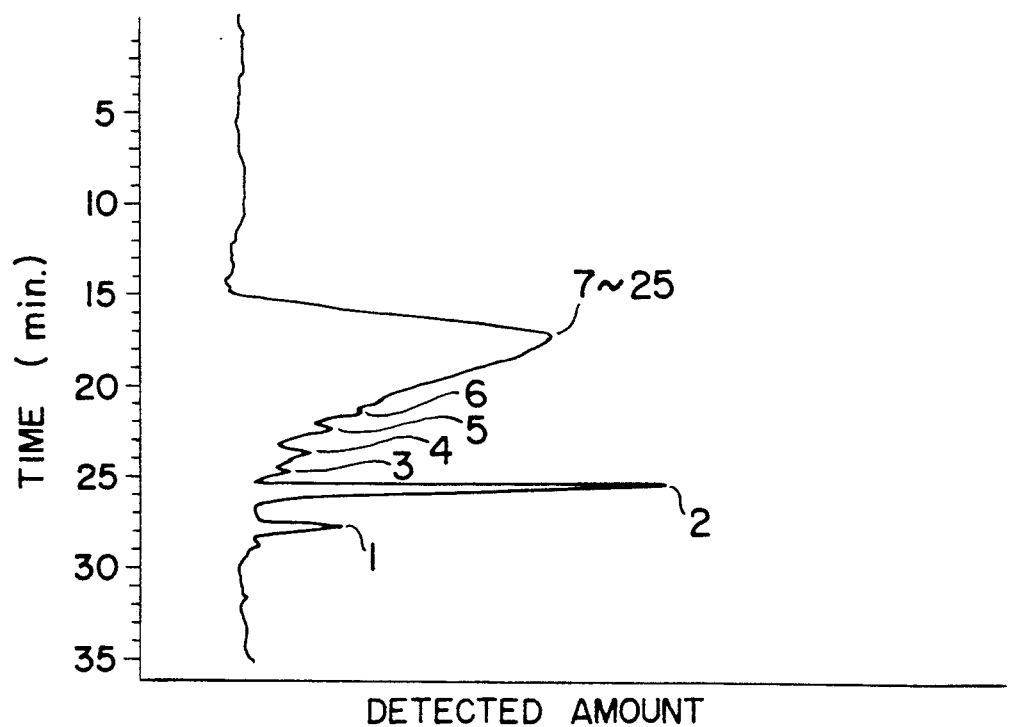

The precipitates obtained were analyzed by high performance liquid chromatography to obtain the results shown in FIG. 4. The precipitates were found to contain 2.1% of monosaccharides, 9.8% of disaccharides, 1.1% of trisaccharides, 3.1% of tetrasaccharides, 0.8% of pentasaccharides, 0.4% of hexasaccharides and 79.3% of 7-25 saccharides. The yield of the precipitates obtained was 26.6 g, which corresponded to 27% of the theoretical yield.

Figure 5:
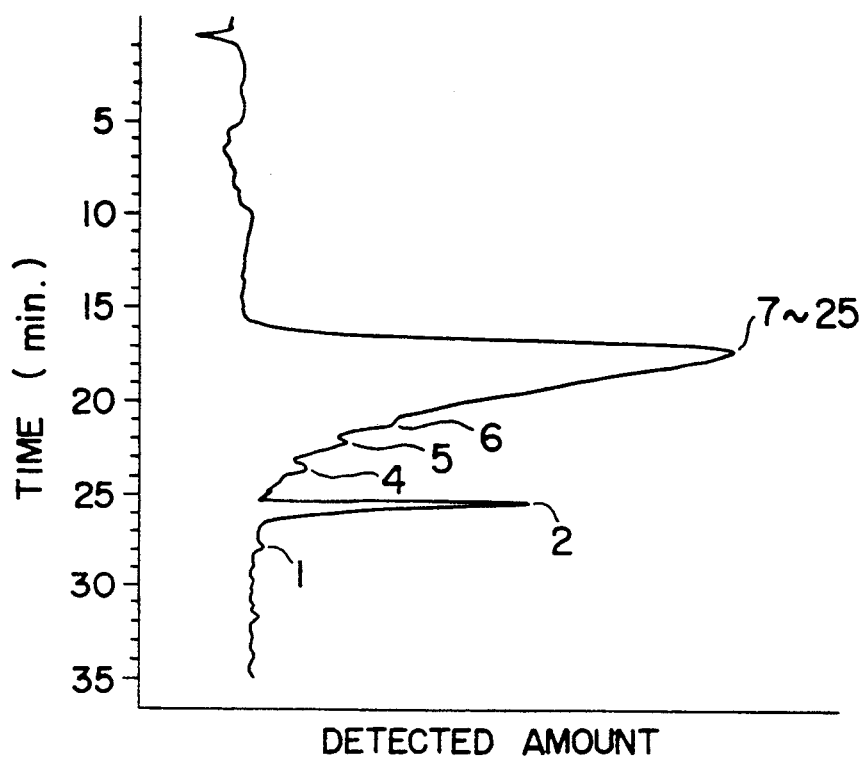

To the above filtrate were further added 4 liters of methanol to effect precipitation again, the precipitates were filtered and washed with acetone. The precipitates obtained were analyzed by high performance liquid chromatography to obtain the results shown in FIG. 5. The precipitates were found to contain 0.1% of monosaccharides, 2.1% of disaccharides, 0.7% of tetrasaccharides, 0.6% of pentasaccharides, 0.3% of hexasaccharides and 79.1% of 7-25 saccharides. The yield of the product was 11.2 g, which corresponded to 12% of the theoretical yield.

The filtrate after reprecipitation as described above was concentrated to 200 milliliters and to the concentrate was added a mixture of methanol (300 milliliters)-acetone (500 milliliters) to obtain precipitates. The precipitates were filtered and washed with acetone.

Figure 6:
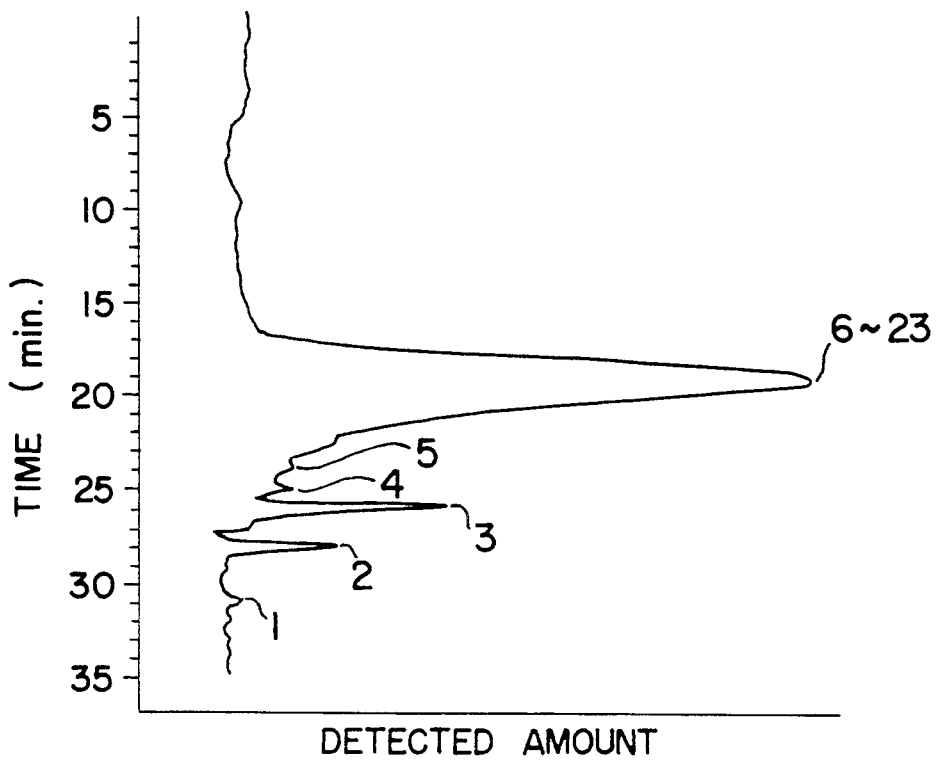

The precipitates were analyzed by high performance liquid chromatography to obtain the results shown in FIG. 6. The precipitates contained 2.3% of monosaccharides, 4.4% of disaccharides, 0.6% of trisaccharides, 0.3% of tetrasaccharides, 0.2% of pentasaccharides and 88.7% of 6-23 saccharides.

The yield of the precipitates obtained was 11.2 g, which corresponded to 12% of the theoretical amount.

Therefore, the total yield was 52.9 g, which corresponded to 54% of the theoretical yield 97.2 g.

Example 4

Into a glass flask of 5 liter inner volume equipped with a stirrer was charged 50 g of a chitosan in flakes of 30 mesh pass, and 480 milliliters of 10% aqueous acetic acid were added thereto little by little under stirring to dissolve the chitosan, followed by cooling of the solution in an ice-water bath.

Subsequently, 136 milliliters of 10% aqueous sodium nitrite (nitrous acid/glucosamine residue = molar ratio 0.7) were added to control the hydrogen ion concentration (pH) to 3, and the reaction was carried out at 0° C. under stirring for 16 hours, followed by leaving to stand at room temperature overnight to complete the reaction.

After completion of the reaction, the mixture was neutralized with conc. ammonia water, concentrated under reduced pressure. Further, to the concentrate was gradually added acetone to effect acetone fractionation by precipitating the products in the order from one with larger molecular weight to obtain the results of fractionation shown in Table 1.

TABLE 1

| Kind | Yield | Chitosan oligosaccharide yield |
|---|---|---|
| Monosaccharide (glucosamine) | 49% | |
| Disaccharides | 5% | |
| Trisaccharides | 6% | |
| Tetrasaccharides | 5% | 51% |
| Pentasaccharides | 6% | |
| Hexasaccharides or higher | 29% | |

Example 5

The experiment was carried out according to the same method as in Example 3 except for using a natural chitin in place of chitosan and changing the molar ratio of nitrous acid/glucosamine residue to 0.5 to prepare a chitin oligomer having a 2,5-anhydromannose group, followed further by the reduction reaction to prepare a chitin oligomer having a 2,5-anhydromannitol group.

Figure 10:
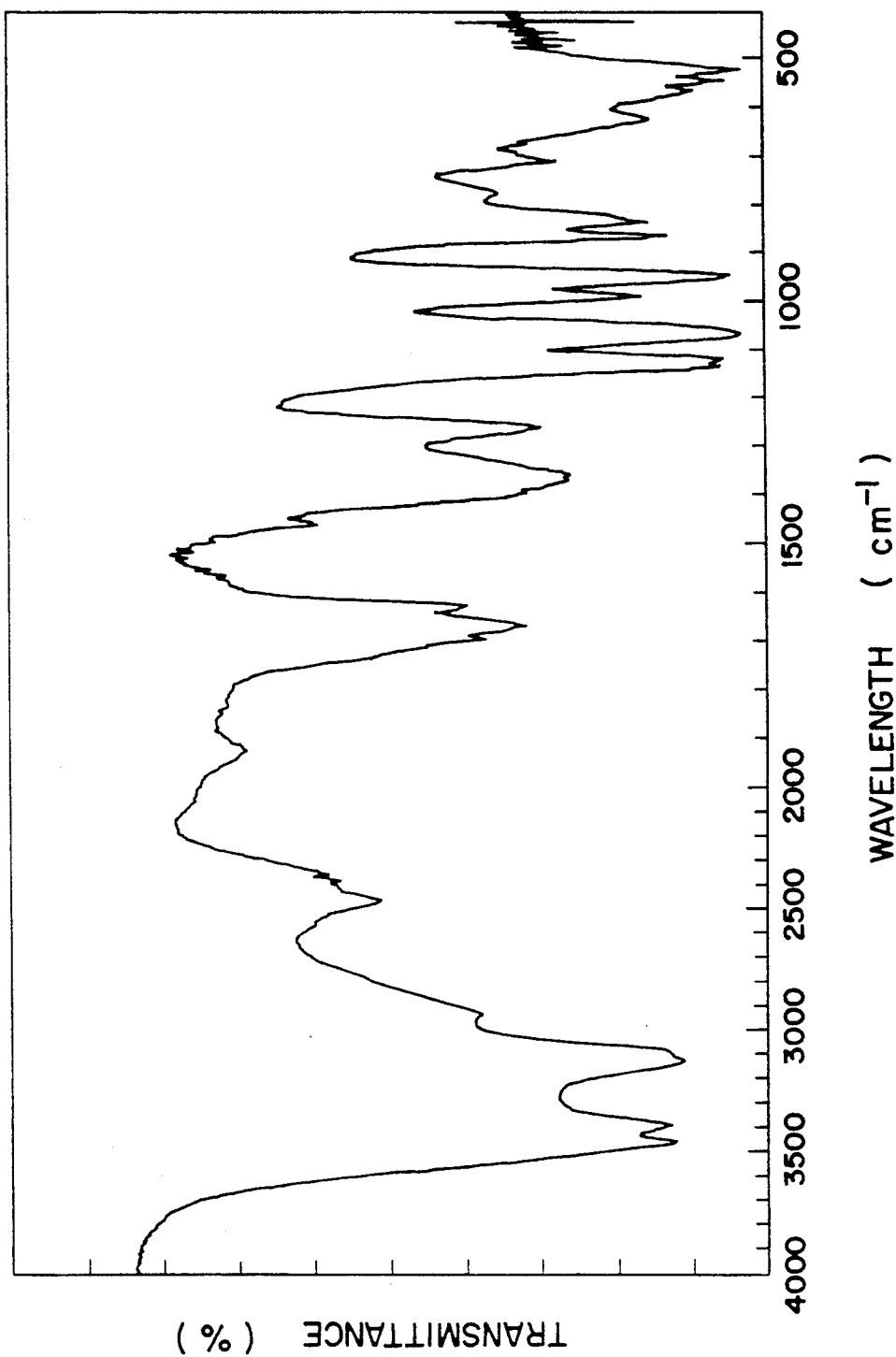

As the result of analysis of the product by high performance liquid chromatography and IR-absorption spectrum analysis, the results as shown in FIG. 10 were obtained. Since an absorption peak is exhibited at the position of 1600-1700 cm$^{-1}$, this was confirmed to be a chitin oligomer having 2,5-anhydromannitol group. Also, said product was confirmed from FIG. 7 to be a chitin oligomer having 2,5-anhydromannitol group which is a mixture of 40-250 saccharides.

Example 6

Into a glass beaker of 500 milliliter inner volume equipped with a stirrer, 10 g of a chitosan in flakes of 30 mesh pass (molecular weight: 40,000) was charged, and to this was added little by little 100 milliliters of aqueous acetic acid (solubilizing agent/water: 10 vol. %), followed by sufficient cooling of the solution in an ice-water bath to 3° C.

Subsequently, 14.5 milliliters of 10% aqueous sodium nitrite (nitrous acid/glucosamine residue in chitosan (molar ratio): 0.5) were added to adjust the hydrogen ion concentration (pH) to 3, and the reaction was carried out in the aqueous solution at 3° C. under stirring for 2 hours to prepare a chitosan oligomer having 2,5-anhydromannose group.

After completion of the reaction, the mixture was neutralized with 15 milliliters of ammonia water, and further with addition of 1.6 g of sodium boronhydride (2-fold moles relative to sodium nitrite), the reduction reaction was carried out by stirring the mixture at room temperature overnight to prepare a chitosan oligomer having 2,5-anhydromannitol.

After completion of the reduction reaction, the reaction mixture was filtered to remove insolubles therefrom, and the filtrate as concentrated to 100 milliliters. Subsequently, the product was precipitated by addition of methanol thereto. In that operation, the amount of methanol employed was changed in terms of concentrate:methanol ratio as 1:3 (first fraction), 1:5 (second fraction), 1:10 (third fraction) to effect fractionation.

Further, concentration was effected to dryness, and the product was precipitated by addition of methanol and acetone. In that operation, fractionation was performed with methanol:acetone of 1:2 (fourth fraction). These precipitates were thoroughly washed with acetone, ether, and dried in a vacuum desiccator.

Figure 9:
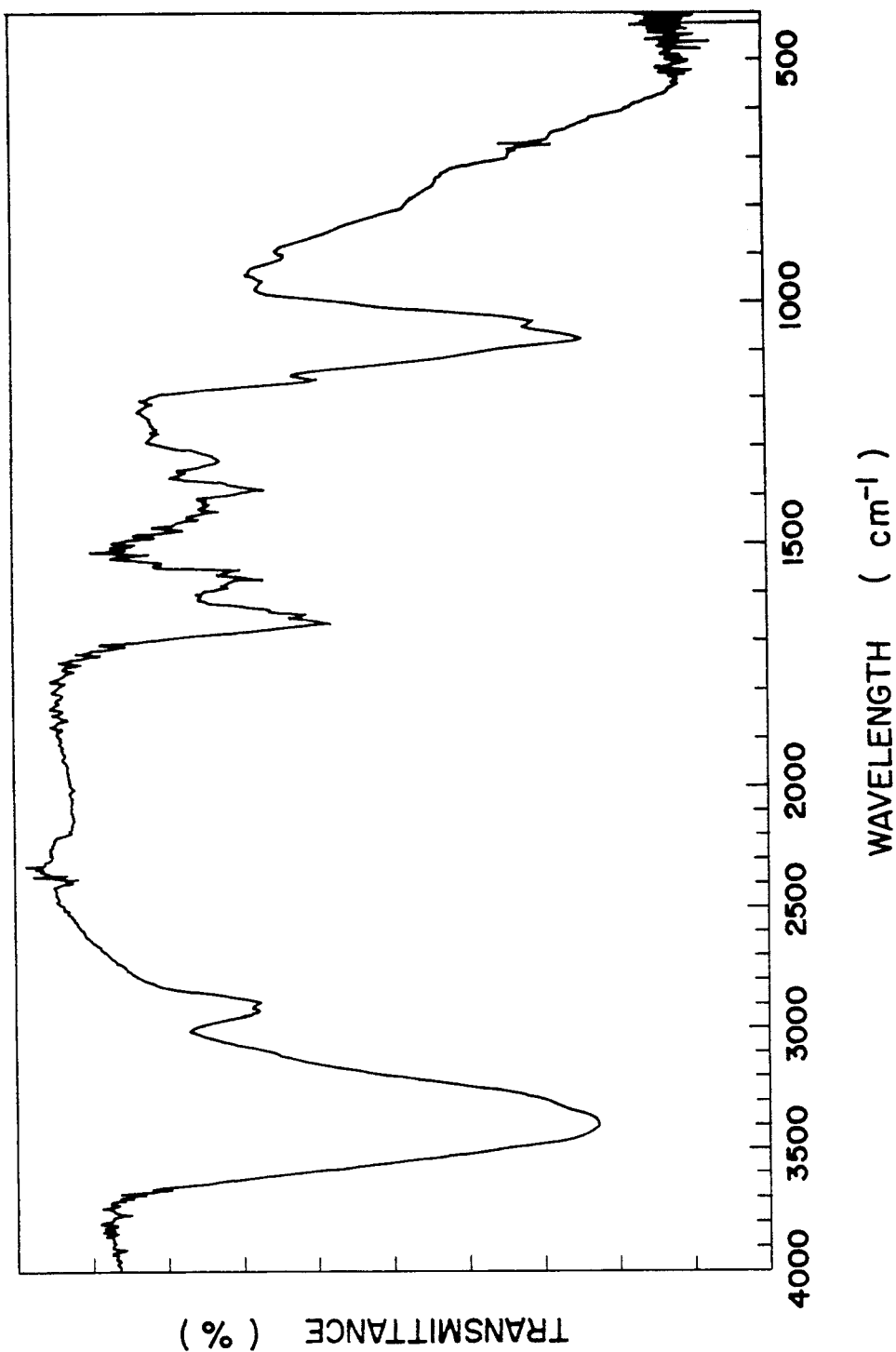

The precipitates were analyzed by IR-ray analysis to obtain the results shown in FIG. 9. The precipitates were found by the IR-ray absorption spectrum analysis to be a chitosan oligomer having 2,5-anhydromannitol group.

The solids of the first to fourth fractions obtained by such fractionation were respectively analyzed by high performance liquid chromatography and elemental analysis.

The analytical conditions in the high performance liquid chromatography analysis were as follows:

Column: Asahipack GFA-30F
Flow rate: 0.3 ml/min.
Temperature: 50° C.
Mobile phase: 0.5 % acetate buffer
pH: 4.0.

The results are shown in FIG. 8(a) to (d).

The products in the respective fractions were found to be as follows.

Figure 8A:
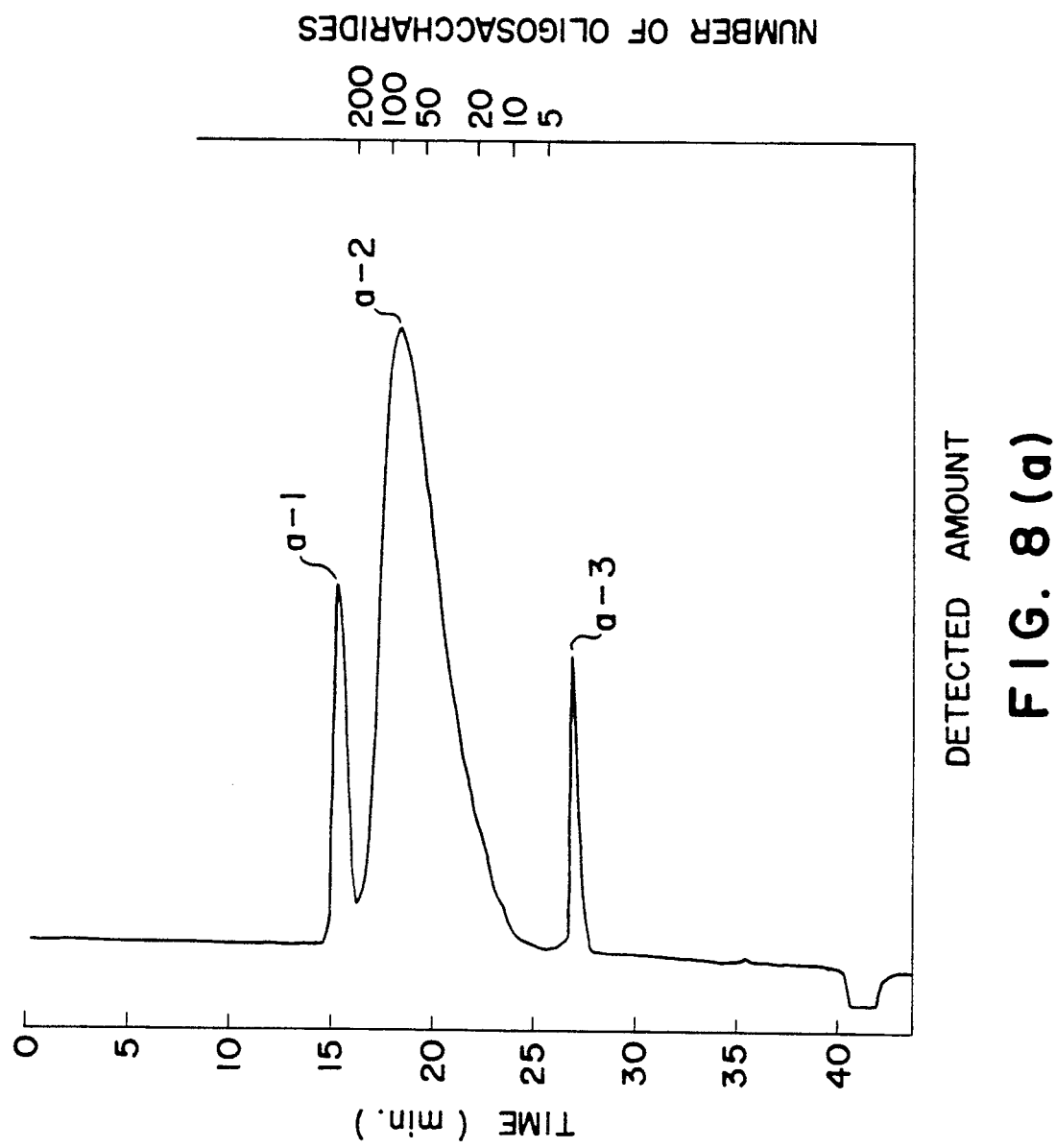
Figure 8B:
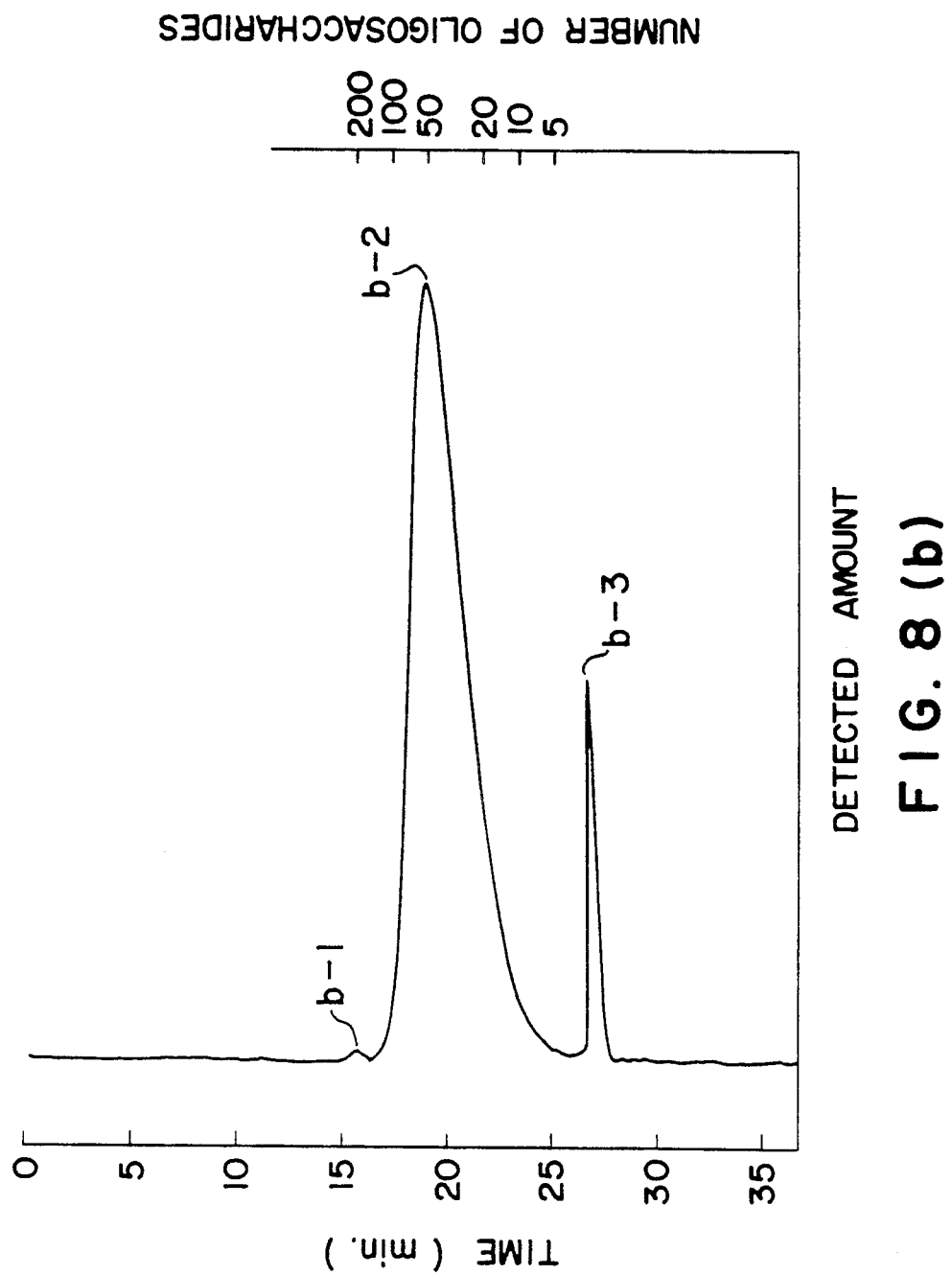
Figure 8C:
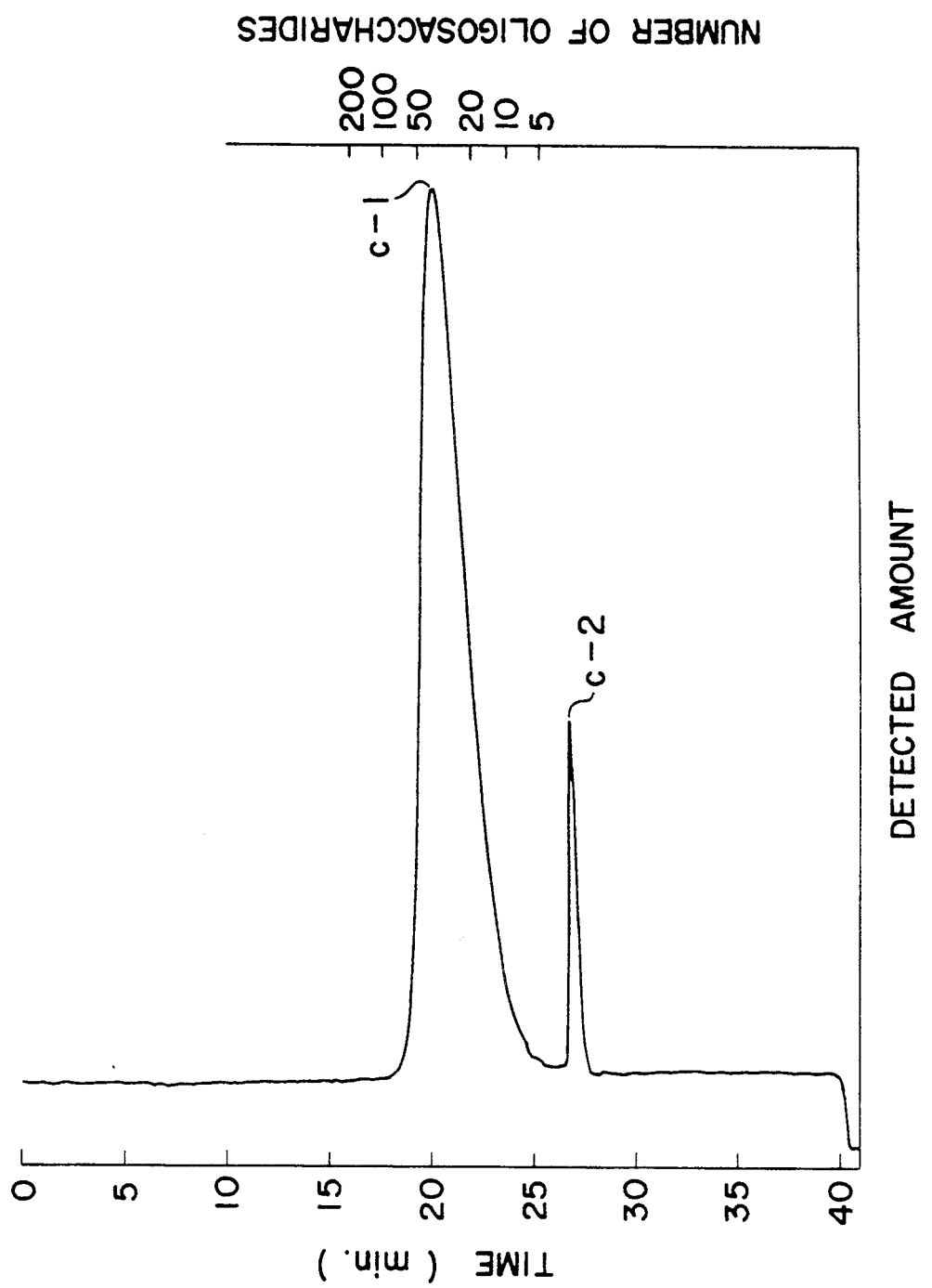
Figure 8:
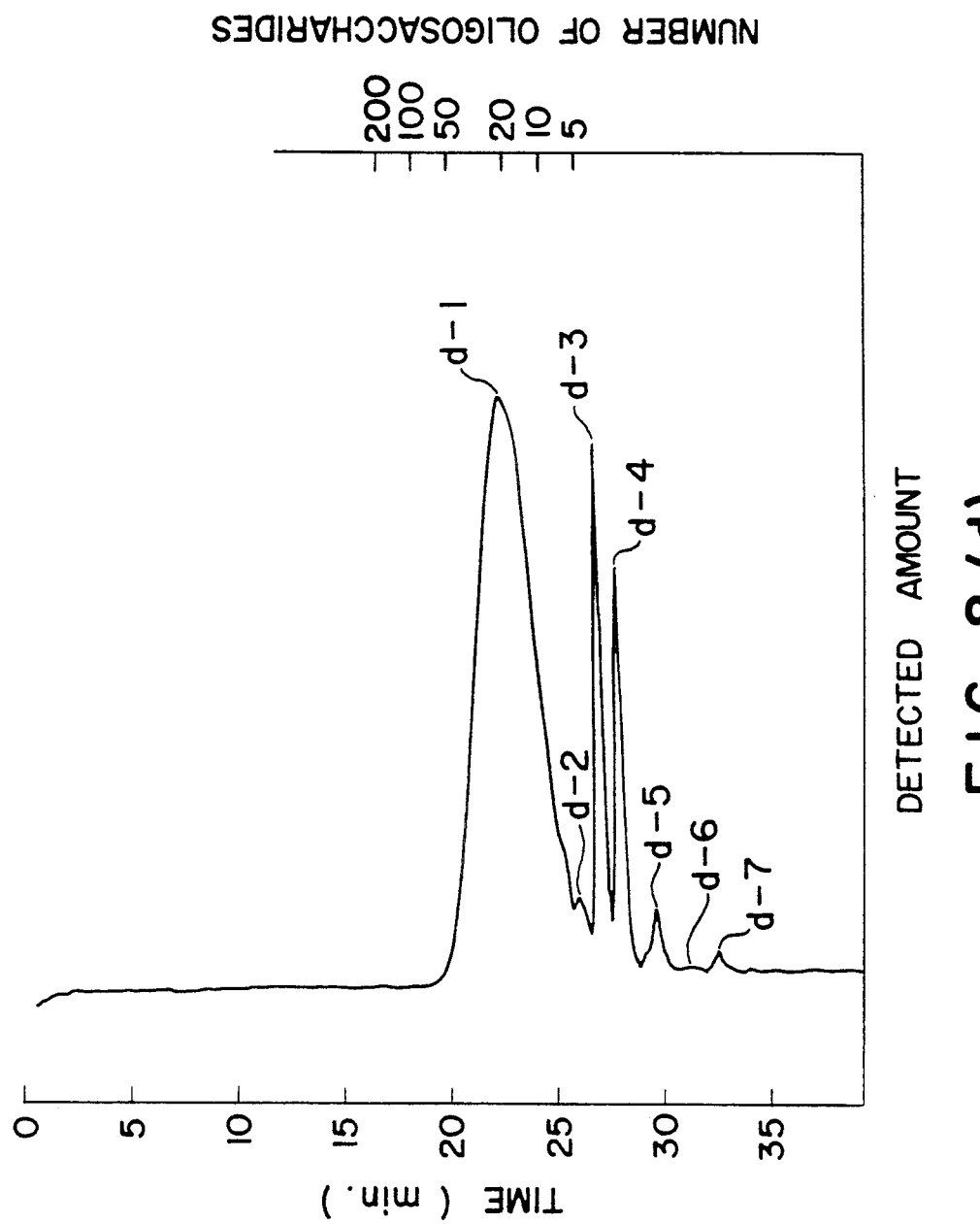

First fraction [FIG. 8(a)]
Yield: 7.2% by weight
Peak a-1: starting material chitosan
Peak a-2: chitosan oligomer 88.5 mole%
Molecular weight: 40,000–1,300 (246 saccharides—7 saccharides)
Peak a-3: sodium acetate
Second fraction [FIG. 8(b)]
Peak b-1: starting material chitosan
Peak b-2: chitosan oligomer 99.7 mole%
Molecular weight: 45,000–1,300 (277 saccharides—7 saccharides)
Peak b-3: sodium acetate
Third fraction [FIG. 8(c)]
Yield: 8.4% by weight
Peak c-1: chitosan oligomer 100 mole%
Molecular weight: 25,000–1,000 (154 saccharides—5 saccharides)
Peak c-2: sodium acetate
Fourth fraction [FIG. 8(d)]
Yield: 42.2% by weight
Peak d-1: chitosan oligomer 97.4 mole %
Molecular weight: 25,000–1,300 (154 saccharides—7 saccharides)
Peak d-2: chitosan oligomer 2.6 mole %
Molecular weight: 1,300–900 (7 saccharides—5 saccharides)
Peak d-3 - 7: various salts.

4. BRIEF DESCRIPTION OF THE DRAWINGS

Figure 7:
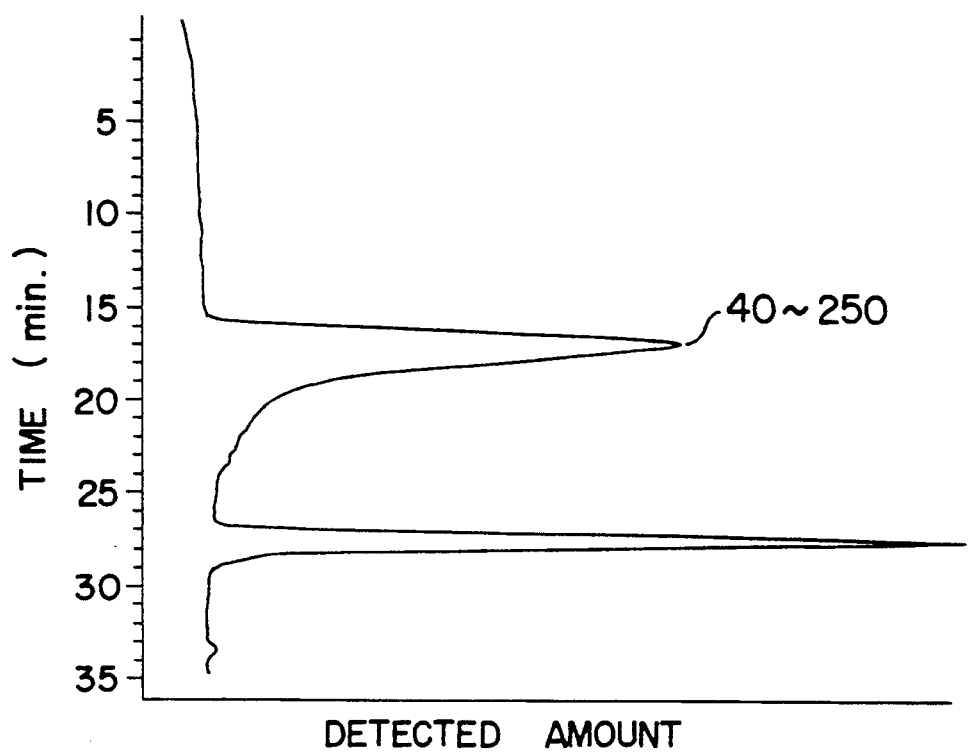

FIGS. 1 to 6 are charts drawn as a result of high performance liquid chromatography analysis of the chitosan oligomers prepared in the examples of the present invention; FIG. 7 is a chart drawn as a result of high performance liquid chromatography analysis of the chitin oligomer prepared in the example of the present invention; FIGS. 8(a) to (d) are charts drawn as a result of high performance liquid chromatography analysis of the respective components of the chitosan oligomer collected by fractionation in the examples of the present invention; FIG. 9 is a chart drawn as a result of IR-ray absorption spectrum analysis of the chitosan oligomer obtained in the example of the present invention; FIG. 10 is a chart drawn as a result of IR-ray absorption spectrum analysis of the chitin oligomer obtained in the example of the present invention.

The numbers set forth in the figures correspond to the following:

1: monosaccharide, 2: disaccharide, 3: trisaccharide, 4: tetrasaccharide, 5: pentasaccharide, 6: hexasaccharide, 6–23: 6–23 saccharides, 7–25: 7–25 saccharides, 8–29: 8–29 saccharide, 10–25: 10–25 saccharides, 40–250: 40–250 saccharides.

What is claimed is:

1. A method for preparing a chitin oligomer or a chitosan oligomer having a 2,5-anhydromannitol group at a terminal end, which comprises reacting chitin or chitosan with nitrous acid at a temperature of 10° C. or lower in an aqueous solution with a pH of 2 to 4 to effect a deamination reaction and pinacol rearrangement and thereby produce a chitin or chitosan oligomer having a 2,5-anhydromannose group at a terminal end, then reducing said chitin oligomer or chitosan oligomer having a 2,5-anhydromannose group at a terminal end with a reducing agent, precipitating and recovering said chitin or chitosan oligomer.

2. A method for preparing a chitin oligomer or a chitosan oligomer having a 2,5-anhydromannitol group at a terminal end according to claim 1, wherein the reducing agent is a boron hydride compound.

3. The method for preparing a chitin oligomer or a chitosan oligomer having a 2,5-anhydromannitol group at a terminal end according to claim 1, wherein an organic acid is present during the reaction with nitrous acid, before the reduction the nitrous acid reaction mixture is neutralized by addition of ammonia, an alkylamine or an ion exchange resin and the reducing agent is a boron hydride.

4. A method for preparing a chitin oligomer or a chitosan oligomer having a 2,5-anhydromannitol group at a terminal end according to claim 1, wherein neutralization is effected by addition of ammonia, an alkylamine or anion exchange resin before carrying out reduction.

5. A method for preparing a chitin oligomer or a chitosan oligomer having a 2,5-anhydromannitol group at a terminal end according to claim 4, wherein after the reduction, by mixing with a medium which is compatible with an aqueous medium and in which the chitin oligomer or the chitosan oligomer is difficulty soluble, the chitin oligomer or chitosan oligomer having a 2,5-anhydromannitol group dissolved in said aqueous medium is precipitated.

6. A chitin oligomer having a 2,5-anhydromannitol group at a terminal end, consisting essentially of a 2,5-anhydromannitol group of the formula:

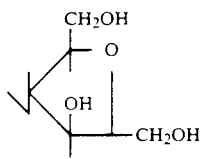

at one end and a group of the structural formula:

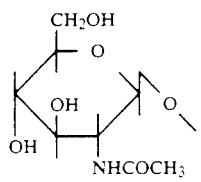

at the other end, both of the end groups being bonded through a chain of 40 to 250 units of the following structural formula a):

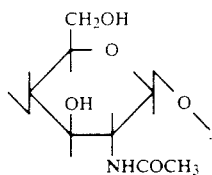

and units of the following structural formula b) in an amount of 0 to 50% of units a):

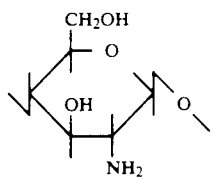

7. A chitosan oligomer having a 2,5-anhydromannitol group at a terminal end, consisting essentially of a 2,5-anhydromannitol group of the formula:

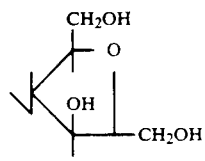

at one end a group of the structural formula:

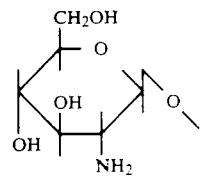

at the other end, both of the end groups being bonded through a chain of 0 to 300 units of the following structural formula a):

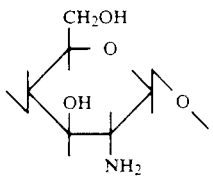

and units of the following structural formula b) in an amount of 0 to 50% of units a):

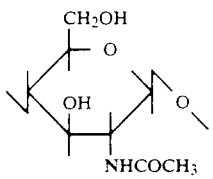

wherein when the chain contains 0 units of a), the end groups are bonded directly to each other.

* * * * *